US012778678B2

(12) United States Patent
Hindi et al.

(10) Patent No.: US 12,778,678 B2
(45) Date of Patent: Nov. 3, 2026

(54) SURGICAL STAPLER RELOAD SIMULATION

(71) Applicant: Cilag GmbH International, Zug (CH)

(72) Inventors: Roberta Hindi, Zug (CH); Chad Prather, Zug (CH)

(73) Assignee: Cilag GmbH International, Zug (CH)

( * ) Notice: Subject to any disclaimer, the term of this patent is extended or adjusted under 35 U.S.C. 154(b) by 1253 days.

(21) Appl. No.: 17/710,226

(22) Filed: Mar. 31, 2022

(65) Prior Publication Data

US 2022/0338931 A1 Oct. 27, 2022

Related U.S. Application Data

(60) Provisional application No. 63/180,598, filed on Apr. 27, 2021.

(51) Int. Cl.

*A61B 34/10* (2016.01)
*G06F 3/04842* (2022.01)
*G06F 30/20* (2020.01)

(52) U.S. Cl.

CPC .......... *A61B 34/10* (2016.02); *G06F 3/04842* (2013.01); *G06F 30/20* (2020.01); *A61B 2034/104* (2016.02); *A61B 2034/105* (2016.02); *A61B 2034/107* (2016.02)

(58) Field of Classification Search

CPC ....................................................... G06F 30/20
USPC .............................................................. 703/6
See application file for complete search history.

(56) References Cited

U.S. PATENT DOCUMENTS

2010/0198402 A1* 8/2010 Greer ......................... B25J 3/04 901/41
2021/0196425 A1* 7/2021 Shelton, IV ....... A61B 1/00193

OTHER PUBLICATIONS

Huang_2015 (A thickness Calibration Device is Needed to Determine Staple Height and Avoid Leaks in Laparascopic Sleeve Gastrectomy, Obes Surg (2015)). (Year: 2015).*
Henderson_2017 (Add a Slider to your chart in Excel, Youtube.com May 1, 2017). (Year: 2017).*

* cited by examiner

*Primary Examiner* — Brian S Cook
(74) *Attorney, Agent, or Firm* — Condo Roccia Koptiw LLP

(57) ABSTRACT

A device for simulating a surgical activity may present a first graphical representation of a portion of anatomy. The device may simulate a path for the surgical activity. The device may determine surgical tool selection points associated with selecting surgical tools on the path for the surgical activity. The device may present a surgical range to select from at surgical tool selection points. In response to receiving an indication of the selected surgical range, the device may simulate a surgical outcome associated with selecting a surgical tool at the surgical tool selection point. In response to receiving an indication of the selected surgical tool, the device may generate the selected surgical tool at the surgical tool selection point.

20 Claims, 8 Drawing Sheets

SURGICAL STAPLER RELOAD SIMULATION

CROSS-REFERENCE TO RELATED APPLICATIONS

This application claims the benefit of Provisional U.S. Patent Application No. 63/180,598, filed Apr. 27, 2021, the disclosure of which is incorporated herein by reference in its entirety.

BACKGROUND

Surgical simulations, such as computer-based, two-dimensional or three-dimensional simulations of a surgical environment and/or surgical procedure for example, present an opportunity to advance the surgical arts. Surgical simulations have potential to benefit surgical training, planning, development, and the like. For example, surgical simulations may be used to train surgeons in new procedures and/or to improve the performance of procedures they already know. Surgical simulations may be used as a virtual "dress rehearsal" to help a surgeon prepare for an upcoming procedure. And surgical simulations may be used to experiment with unproven procedures and techniques.

SUMMARY

A device and method disclosed herein may enable improved surgical planning. For example, identifying for a particular surgical procedure both the appropriate staple cartridges to employ and the respective locations for their use may enable improved surgical planning.

A device for simulating a surgical activity may present a first graphical representation of a portion of anatomy. The device may simulate a path for the surgical activity via a second graphical representation. The path may be a cutting path. The path may be superimposed over the graphical representation of the anatomy. In examples, the device may present a graphical user interface configured to enable a user to draw on the graphical representation of the portion of anatomy. The device may receive an indication from the user of the drawn path on the first graphical representation of the portion of anatomy. The device may superimpose the drawn path over the first graphical representation of the portion of anatomy. In examples, the device may segment the path into six segments based on the simulated path for the surgical activity via the second graphical representation. The device may identify a starting point and five intersection points between the six segments. The starting point and five intersection points may be the surgical tool selection points. The device may receive an indication of a selected surgical tool from the surgical tools at a surgical tool selection point. In response to receiving the indication of the selected surgical tool, the device may associate the selected surgical tool at the surgical tool selection point. The device may thus obtain surgical tool selections at the surgical tool selection points.

The device may determine surgical tool selection points associated with selecting surgical tools on the path for the surgical activity. In examples, the surgical tools may be various types of surgical staple cartridges. The device may present a surgical range to select from at a surgical tool selection point. In examples, the surgical range may be a tissue thickness range. The device may receive an indication of a selected surgical range. In examples, device may present a first axis configured to represent the surgical range to select from. The first axis may include a slider. The selected surgical range, which may include an upper bound value and a lower bound value, may be received via the slider. In response to receiving the indication of the selected surgical range (e.g., via the slider), the device to present a visual representation of the surgical tools that are suitable for selection.

The device may provide a visual indication of the surgical tools in response to receiving the indication of the selected surgical range. In examples, the device may generate a graphical representation of at least one suitable surgical tool. The surgical tools may be presented along the second axis (e.g., the horizontal axis), which may be associated with an optimal tissue thickness range. The tissue thickness range for the surgical tools may include a lower limit and an upper limit, corresponding to the surgical range presented along the first axis (e.g., the vertical axis). The tissue thickness range for the surgical tools may help the user to select at least one of the surgical tools based on the selected surgical range (e.g., the selected tissue thickness range). Depending on the desired surgical outcome (e.g., the perfusion preference) of the user, the user may select their preferred surgical tool.

In response to receiving the indication of the selected surgical range (e.g., via the slider), the device may simulate a surgical outcome associated with selecting a surgical tool at the surgical tool selection point. In examples, the surgical outcome may be a perfusion outcome associated with selecting a stapler cartridge type at a selected tissue thickness range. The device may present the surgical tools on a second axis. The device may receive an indication of a selected surgical tool. In response to receiving the indication of the selected surgical tool at the surgical tool selection point, the device 100 may generate a surgical plan for the selection points on the path for performing the surgical activity. The device may generate a control signal that may be generated for performing the surgical activity along the path. The control signal may include an indication of the selected surgical tools at the surgical tool selection points. The control signal may include the surgical plan for the surgical tool selection points on the path for performing the surgical activity. The control signal may be sent to a surgical control system. In examples, the control signal may be configured to prompt the surgeon or the surgeon's assistant to use the appropriate surgical tools at the responding surgical tool selection points.

In examples, the device may obtain a reinforcement range associated with the selected surgical range. The device may calculate a reinforced surgical range based on the selected surgical range and the reinforcement range. The simulated surgical outcome may be determined based on the reinforced surgical range. In examples, the device may present a second set of surgical tools to select from at the selected surgical tool selection point (e.g., the first set of surgical tool being the original set of surgical tools) based on the reinforced surgical range. In response to receiving the indication of the selected surgical range, the device may simulate a surgical outcome associated with selecting a second set of surgical tools at the surgical tool selection point. The device may receive an indication of a selected second surgical tool. In response to receiving the indication of the selected second surgical tool, the device may generate the selected second surgical tool at the surgical tool selection point. The device may convert the selected second surgical tool at the surgical tool selection point to a first surgical tool at the surgical tool selection point.

DETAILED DESCRIPTION

Figure 1:
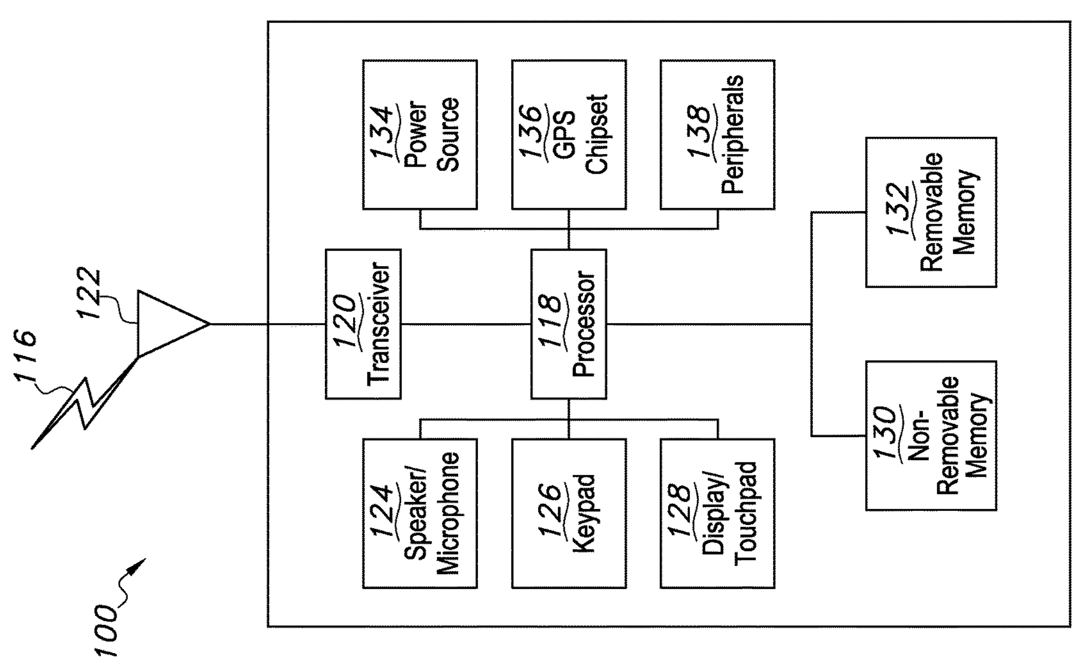
FIG. 1 is a system diagram illustrating an example computing device for simulating a surgical activity.

A device and method disclosed herein may enable improved surgical planning. For example, identifying for a particular surgical procedure both the appropriate staple cartridges to employ and the respective locations for their use may enable improved surgical planning.

A device for simulating a surgical activity may present a first graphical representation of a portion of anatomy. The device may simulate a path for the surgical activity via a second graphical representation. The path may be a cutting path. The path may be superimposed over the graphical representation of the anatomy. In examples, the device may present a graphical user interface configured to enable a user to draw on the graphical representation of the portion of anatomy. The device may receive an indication from the user of the drawn path on the first graphical representation of the portion of anatomy. The device may superimpose the drawn path over the first graphical representation of the portion of anatomy. In examples, the device may segment the path into six segments based on the simulated path for the surgical activity via the second graphical representation. The device may identify a starting point and five intersection points between the six segments. The starting point and five intersection points may be the surgical tool selection points. The device may receive an indication of a selected surgical tool from the surgical tools at a surgical tool selection point. In response to receiving the indication of the selected surgical tool, the device may associate the selected surgical tool at the surgical tool selection point. The device may thus obtain surgical tool selections at the surgical tool selection points.

The device may determine surgical tool selection points associated with selecting surgical tools on the path for the surgical activity. In examples, the surgical tools may be various types of surgical staple cartridges. The device may present a surgical range to select from at a surgical tool selection point. In examples, the surgical range may be a tissue thickness range. The device may receive an indication of a selected surgical range. In examples, device may present a first axis configured to represent the surgical range to select from. The first axis may include a slider. The selected surgical range, which may include an upper bound value and a lower bound value, may be received via the slider. In response to receiving the indication of the selected surgical range (e.g., via the slider), the device to present a visual representation of the surgical tools that are suitable for selection.

The device may provide a visual indication of the surgical tools in response to receiving the indication of the selected surgical range. In examples, the device may generate a graphical representation of at least one suitable surgical tool. The surgical tools may be presented along the second axis (e.g., the horizontal axis), which may be associated with an optimal tissue thickness range. The tissue thickness range for the surgical tools may include a lower limit and an upper limit, corresponding to the surgical range presented along the first axis (e.g., the vertical axis). The tissue thickness range for the surgical tools may help the user to select at least one of the surgical tools based on the selected surgical range (e.g., the selected tissue thickness range). Depending on the desired surgical outcome (e.g., the perfusion preference) of the user, the user may select their preferred surgical tool.

In response to receiving the indication of the selected surgical range (e.g., via the slider), the device may simulate a surgical outcome associated with selecting a surgical tool at the surgical tool selection point. In examples, the surgical outcome may be a perfusion outcome associated with selecting a stapler cartridge type at a selected tissue thickness range. The device may present the surgical tools on a second axis. The device may receive an indication of a selected surgical tool. In response to receiving the indication of the selected surgical tool at the surgical tool selection point, the device 100 may generate a surgical plan for the selection points on the path for performing the surgical activity. The device may generate a control signal that may be generated for performing the surgical activity along the path. The control signal may include an indication of the selected surgical tools at the surgical tool selection points. The control signal may include the surgical plan for the surgical tool selection points on the path for performing the surgical activity. The control signal may be sent to a surgical control system. In examples, the control signal may be configured to prompt the surgeon or the surgeon's assistant to use the appropriate surgical tools at the responding surgical tool selection points.

In examples, the device may obtain a reinforcement range associated with the selected surgical range. The device may calculate a reinforced surgical range based on the selected surgical range and the reinforcement range. The simulated surgical outcome may be determined based on the reinforced surgical range. In examples, the device may present a second set of surgical tools to select from at the selected surgical tool selection point (e.g., the first set of surgical tool being the original set of surgical tools) based on the reinforced surgical range. In response to receiving the indication of the selected surgical range, the device may simulate a surgical outcome associated with selecting a second set of surgical tools at the surgical tool selection point. The device may receive an indication of a selected second surgical tool. In response to receiving the indication of the selected second surgical tool, the device may generate the selected second surgical tool at the surgical tool selection point. The device may convert the selected second surgical tool at the surgical tool selection point to a first surgical tool at the surgical tool selection point.

FIG. 1 is a system diagram illustrating an example computing device 100 for simulating and/or optimizing surgical stapler reload selections. As shown in FIG. 1, the computing device 100 may include a processor 118, a transceiver 121, a transmit/receive element 121, a speaker/microphone 124, a keypad 126, a display/touchpad 128, non-removable memory 131, removable memory 132, a power source 134, a global positioning system (GPS) chipset 136, and/or other peripherals 138, among others. It will be appreciated that the computing device 100 may include any sub-combination of the foregoing elements while remaining consistent with an embodiment.

The processor 118 may be a general-purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 118 may perform signal coding, data processing, power control, input/output processing, and/or any other functionality that enables the computing device 100 to operate in a wireless environment. The processor 118 may be coupled to the transceiver 121, which may be coupled to the transmit/receive element 121. While FIG. 1 depicts the processor 118 and the transceiver 121 as separate components, it will be appreciated that the processor 118 and the transceiver 121 may be integrated together in an electronic package or chip.

The transmit/receive element 121 may be configured to transmit signals to, or receive signals from, a base station over the air interface 116. For example, in one embodiment, the transmit/receive element 121 may be an antenna configured to transmit and/or receive RF signals. In an embodiment, the transmit/receive element 121 may be an emitter/detector configured to transmit and/or receive IR, UV, or visible light signals, for example. In yet another embodiment, the transmit/receive element 121 may be configured to transmit and/or receive both RF and light signals. It will be appreciated that the transmit/receive element 121 may be configured to transmit and/or receive any combination of wireless signals.

The processor 118 of the computing device 100 may be coupled to, and may receive user input data from, the speaker/microphone 124, the keypad 126, and/or the display/touchpad 128 (e.g., a liquid crystal display (LCD) display unit or organic light-emitting diode (OLED) display unit). The processor 118 may also output user data to the speaker/microphone 124, the keypad 126, and/or the display/touchpad 128. In addition, the processor 118 may access information from, and store data in, any type of suitable memory, such as the non-removable memory 131 and/or the removable memory 132. The non-removable memory 131 may include random-access memory (RAM), read-only memory (ROM), a hard disk, or any other type of memory storage device. The removable memory 132 may include a subscriber identity module (SIM) card, a memory stick, a secure digital (SD) memory card, and the like. In other embodiments, the processor 118 may access information from, and store data in, memory that is not physically located on the computing device 100, such as on a server or a home computer (not shown).

The processor 118 may receive power from the power source 134 and may be configured to distribute and/or control the power to the other components in the computing device 100. The power source 134 may be any suitable device for powering the computing device 100. For example, the power source 134 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 118 may also be coupled to the GPS chipset 136, which may be configured to provide location information (e.g., longitude and latitude) regarding the current location of the computing device 100. In addition to, or in lieu of, the information from the GPS chipset 136, the computing device 100 may receive location information over the air interface 116 from a base station and/or determine its location based on the timing of the signals being received from two or more nearby base stations. It will be appreciated that the computing device 100 may acquire location information by way of any suitable location-determination method while remaining consistent with an embodiment.

The processor 118 may further be coupled to other peripherals 138, which may include one or more software and/or hardware modules that provide additional features, functionality and/or wired or wireless connectivity. For example, the peripherals 138 may include an accelerometer, an e-compass, a satellite transceiver, a digital camera (for photographs and/or video), a universal serial bus (USB) port, a vibration device, a television transceiver, a hands free headset, a Bluetooth® module, a frequency modulated (FM) radio unit, a digital music player, a media player, a video game player module, an Internet browser, a Virtual Reality and/or Augmented Reality (VR/AR) device, an activity tracker, and the like. The peripherals 138 may include one or more sensors, the sensors may be one or more of a gyroscope, an accelerometer, a hall effect sensor, a magnetometer, an orientation sensor, a proximity sensor, a temperature sensor, a time sensor; a geolocation sensor; an altimeter, a light sensor, a touch sensor, a magnetometer, a barometer, a gesture sensor, a biometric sensor, and/or a humidity sensor.

The computing device 100 may comprise a processor and a network interface 20100. The processor may be coupled to a communication module, storage, memory, non-volatile memory, and input/output (I/O) interface via a system bus. The system bus can be any of several types of bus structure (s) including the memory bus or memory controller, a peripheral bus or external bus, and or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computing device 100 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computing device 100 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computing device 100 and to output information from the computing device 100 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computing device 100 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computing device 100 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computing device 100, it can also be external to the computing device 100. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

The computing device 100 may be used to perform surgical stapler reload stimulation and/or optimization. For example, reload optimization simulation may be performed for a laparoscopic sleeve gastrectomy procedure.

Figure 2:
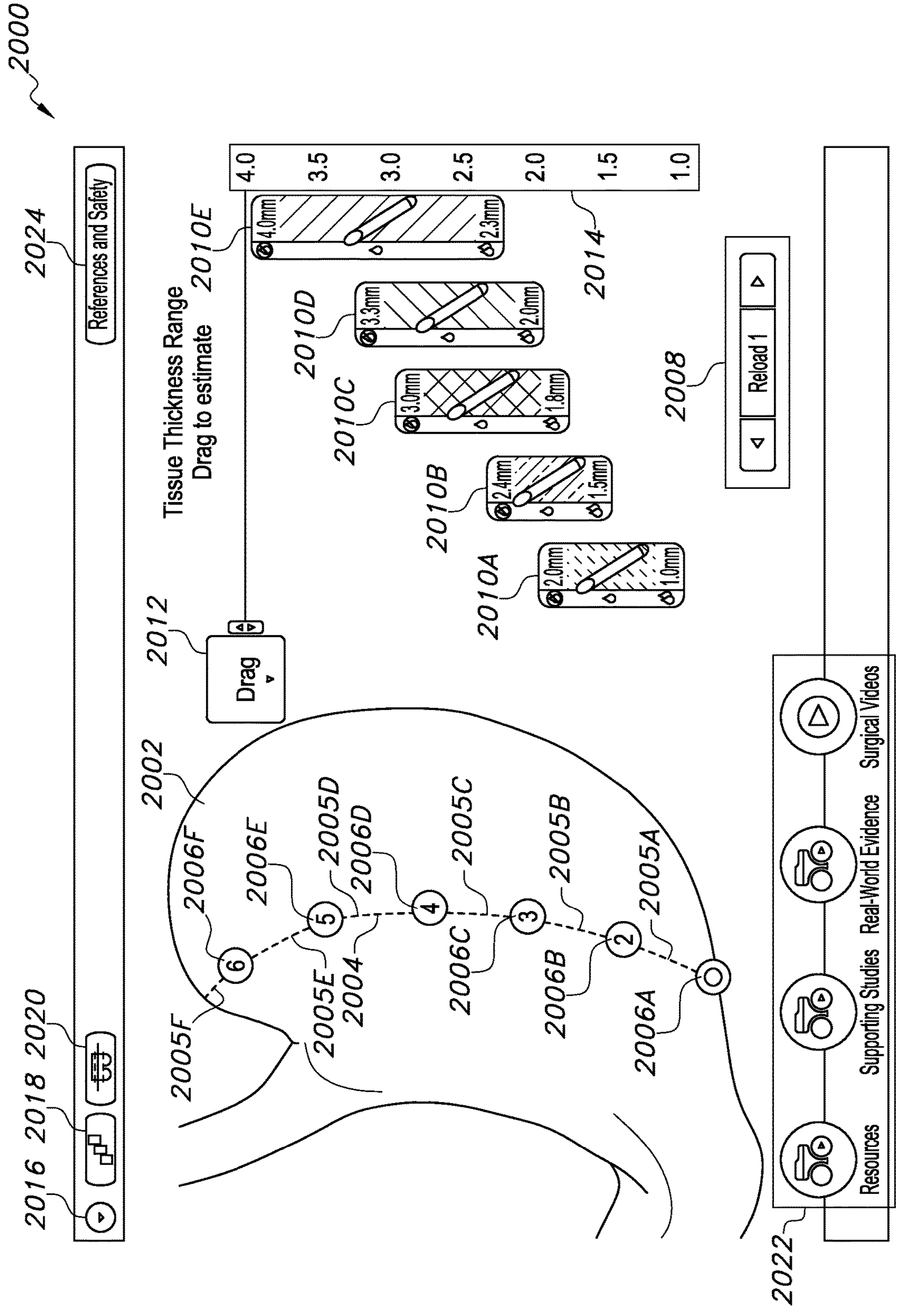
FIG. 2 illustrates an example of a graphical user interface for simulating a surgical activity.

FIG. 2 illustrates an example of a graphical user interface 2000 for simulating a surgical activity. The simulated surgical activity may be selecting a type of surgical stapler cartridge (e.g., surgical stapler reload selections) for a cutting a portion of anatomy. The surgical stapler cartridge type may be selected depending on a tissue thickness range. Different surgical stapler cartridge types are optical for use at different tissue thickness ranges. In examples, a type of stapler cartridge may include long staples which is optimal for use in thicker tissue. In examples, a type of stapler cartridge may include short staples which is optimal for use in thinner tissue. The tissue may correspond to a piece of anatomy, such a portion of a stomach.

The graphical user interface 2000 may be presented via the computing device 100 as described in FIG. 1. The graphical user interface 2000 may include a first graphical representation 2002. The first graphical representation 2002 may represent a portion of anatomy, such as a portion of a stomach. The graphical user interface 2000 may include a path 2004 for simulating the surgical activity. The path 2004 may simulate a path of a laparoscopic sleeve gastrectomy staple line for cutting a portion of anatomy (e.g., a cutting path which may be used by a bariatric surgeon). The path 2004 for the surgical activity may be represented via a second graphical representation. The path 2004 may be superimposed over the first graphical representation 2002 (e.g., the path of the laparoscopic sleeve gastrectomy staple line may be superimposed over the portion of the stomach). Examples of creating the path 2004 on the graphical user interface are described in further detail below in description related to FIGS. 5A-5B.

The device 100 may segment the path 2004 into multiple segments, such as segments 2005A-2005F on the graphical user interface 2000 as shown in FIG. 2. Although six segments are shown in FIG. 2, the path 2004 may be segmented into any number of segments. Each of the segments 2005A-2005F may be separated by a starting point (e.g., "1" in FIG. 2) and five intersection points (e.g., "2-6" in FIG. 2). The identified starting point and five intersection points may be surgical tool selection points 2006A-2006F, as shown in FIG. 2. Although six surgical tool selection points are shown in FIG. 2, there may any number of surgical selection points corresponding to any number of segments. For example, segments 2005A and 2005B may be separated by surgical tool selection point 2006B (corresponding to point “2” shown in FIG. 2), segments 2005B and 2005C may be separated by surgical tool selection point 2006C (corresponding to point “3” shown in FIG. 2), etc. Each of the surgical tool selection points 2006A-2006F may represent a point on the first graphical representation 2002 (e.g., the portion of anatomy). For example, surgical tool selection point 2006A may correspond to point “1” in FIG. 2, surgical tool selection point 2006B may correspond to point “2” in FIG. 2, surgical tool selection point 2006C may corresponding to point “3” in FIG. 2, etc. Each of the points on the first graphical representation 2002 (e.g., the portion of anatomy) may be associated with a tissue thickness (e.g., different tissue thicknesses) or other physiological property of the first graphical representation 2002 (e.g., the portion of anatomy). Reference tissue thickness points (not shown in FIG. 2) may be displayed on the first graphical representation 2002 (e.g., the portion of anatomy), which can help the user gauge the tissue thickness at each of the surgical tool selection points 2006A-2006F, and the tissue thickness at certain points or areas on first graphical representation 2002 (e.g., the portion of anatomy).

A user may select a surgical tool selection point of the surgical tool selection points 2006A-2006F on the path 2004 (e.g., surgical tool section point 2006A is selected in FIG. 2). The device 100 may receive an indication of the selected surgical tool selection point of the surgical tool selection points 2006A-2006F on the graphical user interface 2000. In response to receiving the indication, the device may present surgical tools 2010A-2010E to select from at the selected surgical tool selection point. The surgical tools 2010A-2010E may be various staple cartridge types (e.g., surgical stapler reload selections). Each surgical tool may be presented in a different color so the user can easily differentiate between them.

In examples, a user may use the surgical point selector 2008 to select a surgical tool selection point 2006A-2006F. In examples, the selector 2008 may display “Reload 1,” which may correspond to selecting from the surgical tools 2010A-2010E at the surgical tool selection point 2006A. If the user selects the forward arrow on the selector 2008, the selector may display “Reload 2,” which may correspond to selecting a surgical tool 2010A-2010E at the surgical tool selection point 2006B. The user may use the selector 2008 to select from the surgical tools 2010A-2010E at each the surgical tool selection points 2006A-2006F. The user may use the back arrow on the selector 2008 to view a previous selection or make a selection at a lowered number surgical tool selection point 2006A-2006F (e.g., the user may click the back arrow in which the selector 2008 may change from displaying “Reload 2,” which may correspond to selecting from the surgical tools 2010A-2010E at the surgical tool selection point 2006B, to displaying “Reload 1,” which may correspond to selecting from the surgical tools 2010A-2010E at the surgical tool selection point 2006A, etc.).

The device 100 may present a surgical range 2014 to select from at the selected surgical tool selection point 2006A-2006F on the graphical user interface 2000. The surgical range 2014 may represent a tissue thickness range to consider selecting from at the selected surgical tool selection point 2006A-2006F. As shown in FIG. 2, the tissue thickness range may be between 1.0-4.0 mm, although any other tissue thickness range may be presented. The user may select a selected surgical range (e.g., tissue thickness range) associated with the selected surgical tool selection point 2006A-2006F. The user may select the selected surgical range (e.g., tissue thickness range) by dragging a slider 2012 to a desired range, or by other similar methods. The device 100 may present a first axis (e.g., a vertical axis) configured to represent the surgical range 2014 (e.g., tissue thickness range) to select from on the graphical user interface 2000. The first axis may include the slider 2012. The indication of the selected surgical range (e.g., tissue thickness range) may be received via the slider 2012. Based on the selected surgical range (e.g., tissue thickness range) selected via the slider 2012, the device 100 may simulate the surgical outcome 3004A-3004C (e.g., described in FIG. 3) on the graphical user interface 2000 associated with selecting a surgical tool 2010A-2010E. The surgical tools 2010A-2010E may be presented along a second axis (e.g., a horizontal axis) at the surgical tool selection point.

Figure 3:
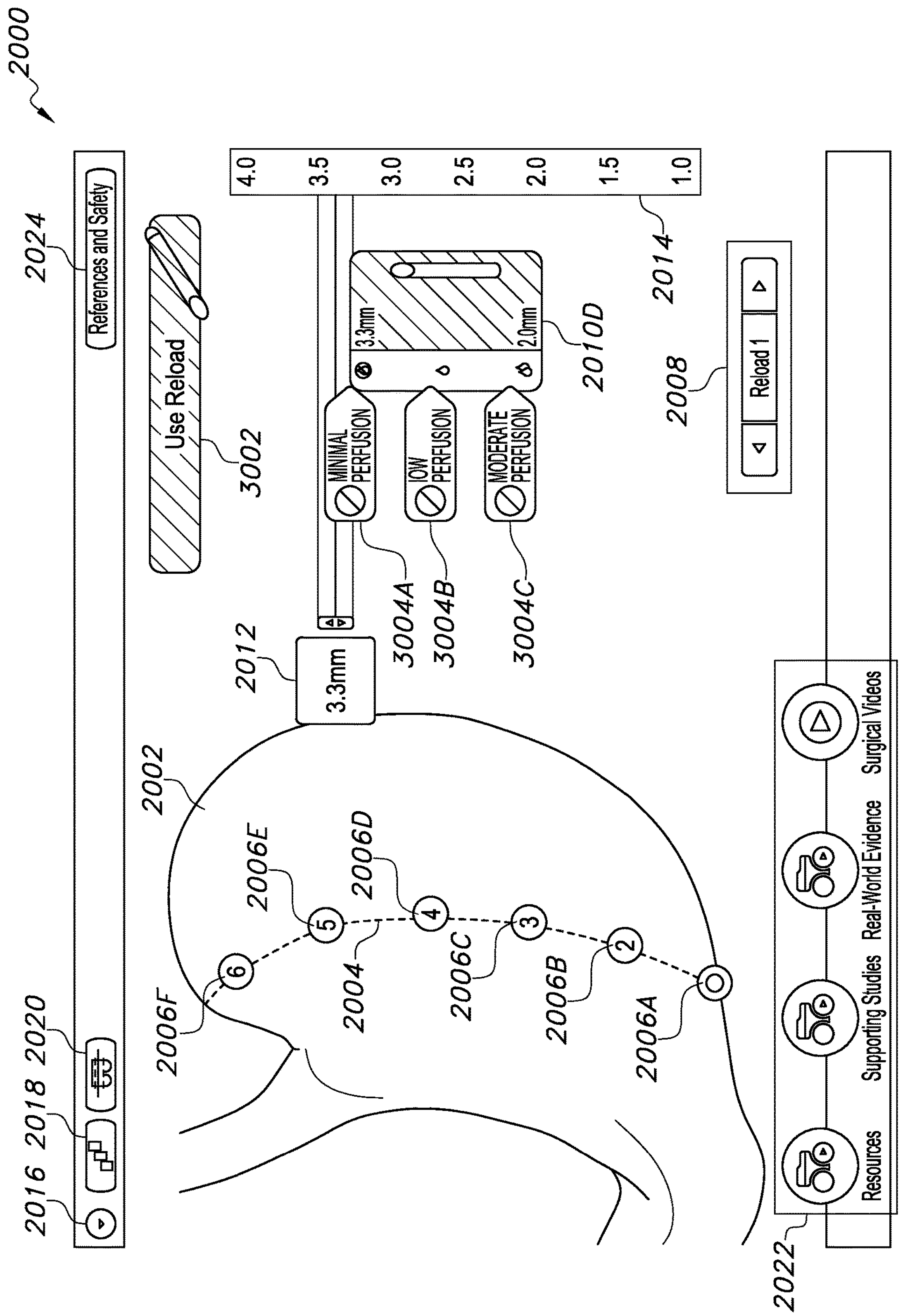
FIG. 3 illustrates an example of simulating a surgical outcome associated with selecting a surgical tool on the graphical user interface.

In response to receiving the indication of the selected surgical range, the device 100 may generate a graphical representation of at least one suitable surgical tool. The device 100 may provide a visual indication of surgical tools 2010A-2010E in response to receiving the indication of the selected surgical range. In examples, the device 100 may generate a graphical representation of at least one suitable surgical tool 2010A-2010E. The surgical tools 2010A-2010E may be presented along the second axis (e.g., the horizontal axis), which may be associated with an optimal tissue thickness range. The tissue thickness range for the surgical tools 2010A-2010E may include a lower limit and an upper limit, corresponding to the surgical range 2014 presented along the first axis (e.g., the vertical axis). The tissue thickness range for the surgical tools 2010A-2010E may help the user to select at least one of the surgical tools 2010A-2010E based on the selected surgical range (e.g., the selected tissue thickness range). For example, the user may select a surgical range (e.g., a tissue thickness range) of 3.3 mm (e.g., as shown in FIG. 3). Based on the selected surgical range (e.g., selected tissue thickness range) of 3.3 mm, the user may be guided to select surgical tool 2010D or surgical tool 2010E since the selected surgical range (e.g., selected tissue thickness range) is within the tissue thickness range of surgical tool 2010D (between 2.0 mm and 3.3 mm as shown in FIG. 2) and within tissue thickness range of surgical tool 2010E (between 2.3 mm and 4.0 mm as shown in FIG. 2). Depending on the desired surgical outcome 3004A-3004C (e.g., the perfusion preference) of the user, the user may select either surgical tool 2010D or surgical tool 2010E, as described in further detail below.

Figure 6:
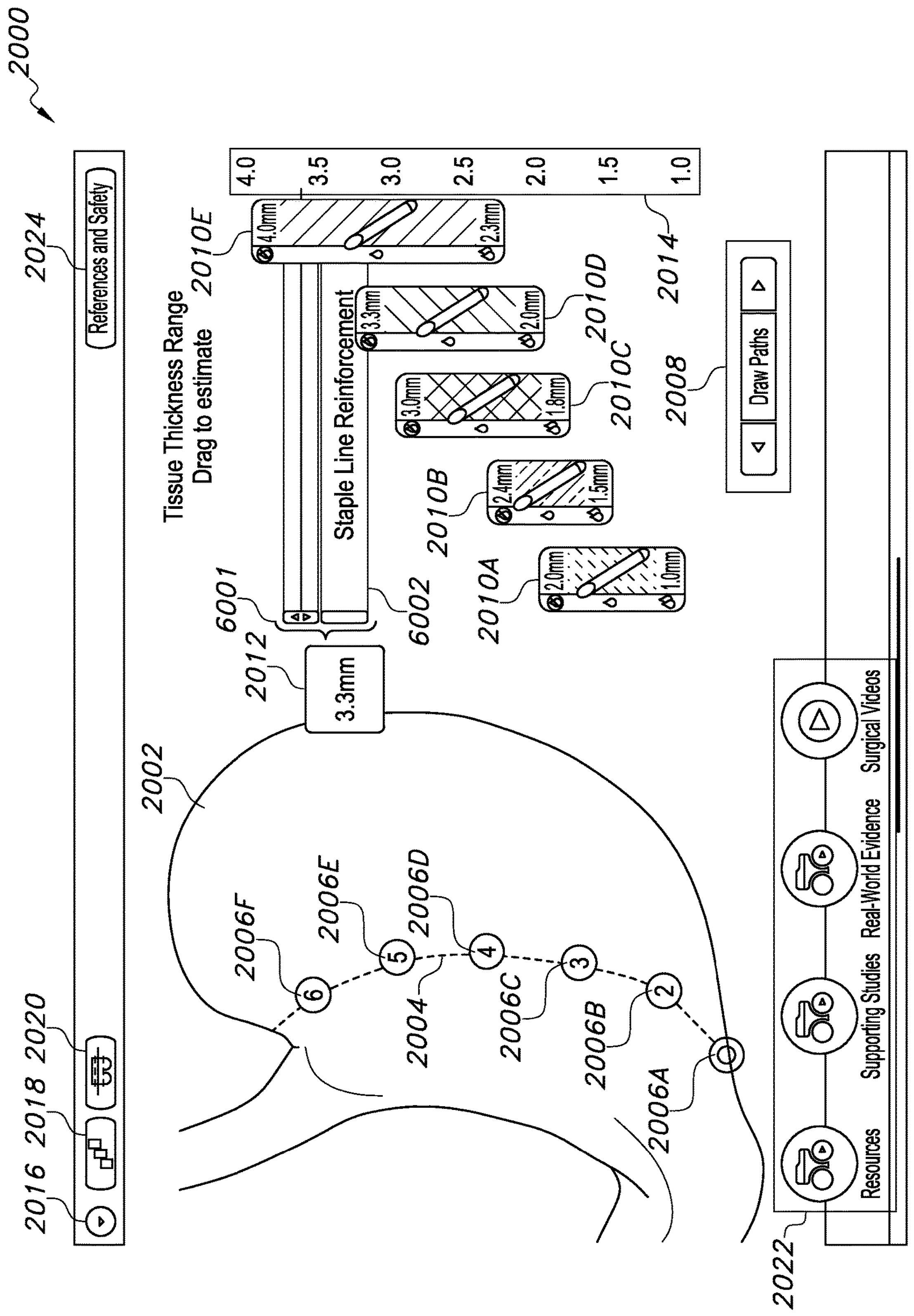
FIG. 6 illustrates an example of simulating a reinforcement range associated with a surgical range on the graphical user interface.
Figure 7:
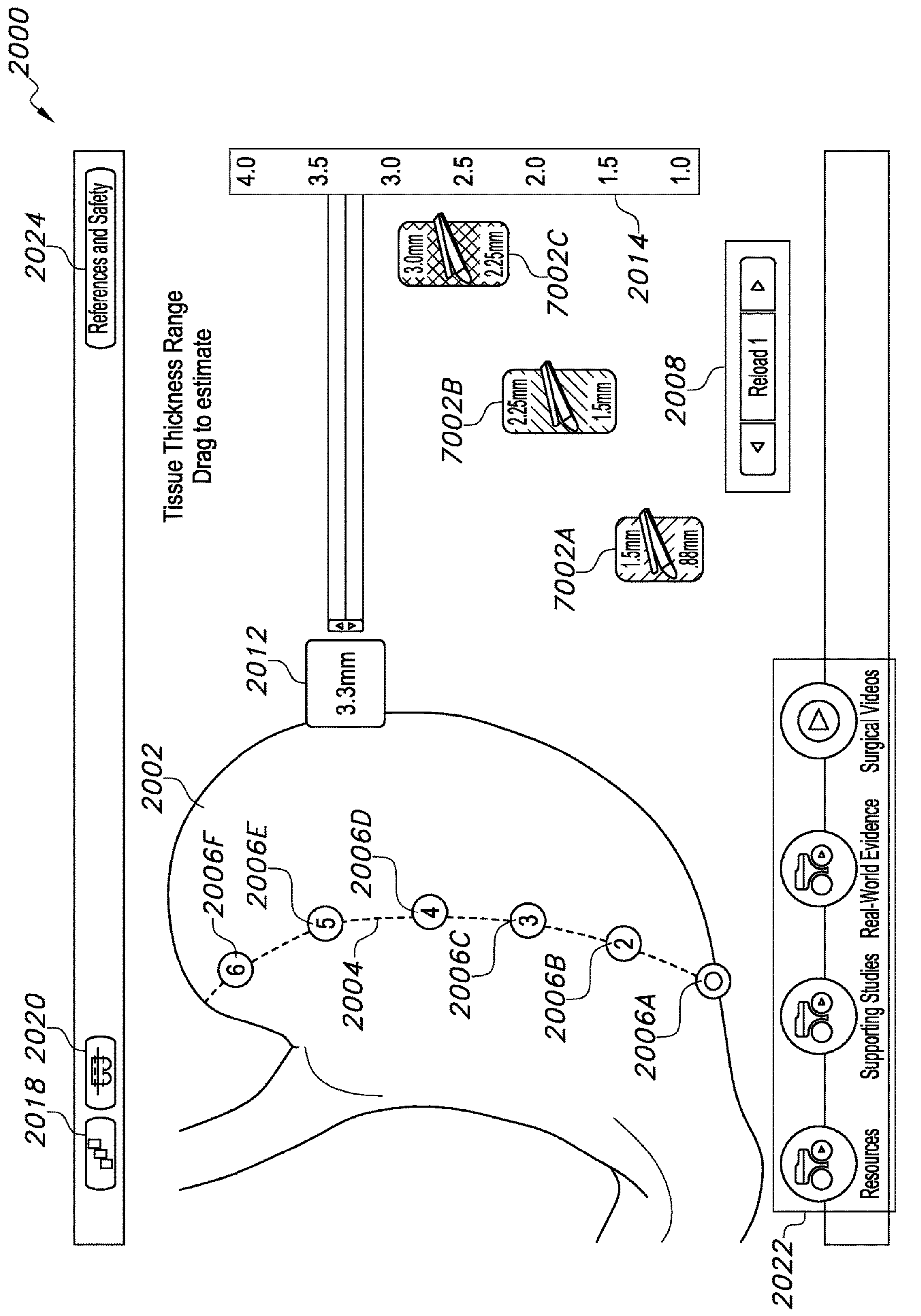
FIG. 7 illustrates an example of presenting a second set of surgical tools to select from on the graphical user interface.

The graphical user interface 2000 may include a navigation control button 2016, an alternative surgical tool toggle 2018, a reinforcement toggle 2020, resource buttons 2022, and a reference and safety button 2024. The navigation control button 2016 may provide a drop down menu for the user to select various menu options for the graphical user interface 2000, such as presentation options, color options, background options, etc. The alternative surgical tool toggle 2018 may trigger the graphical user interface 2000 to present a second set surgical tools 7002A-7002C (as shown in FIG. 7) to select from at the selected surgical tool selection point (e.g., the surgical tools 2010A-2010E being a first set of surgical tools 2010A-2010E), which is described in further detail below. The reinforcement toggle 2020 may trigger the graphical user interface 2000 to calculate a reinforced surgical range 6001 based on the selected surgical range and the reinforcement range 6002 (as shown in FIG. 6), which is described in further detail below. The resource buttons 2022 may include resources related to the simulation of the surgical activity, supporting studies related to the simulation of the surgical activity, real-world evidence related to the simulation of the surgical activity, and/or surgical videos related to the simulation of the surgical activity. The reference and safety button 2024 may include references and safety information for the simulation. Each of the navigation control button 2016, the alternative surgical tool toggle 2018, the reinforcement toggle 2020, the resource buttons 2022, and the reference and safety button 2024 may be presented with different symbols so the user can easily differentiate between them.

FIG. 3 illustrates an example of simulating a surgical outcome associated with selecting a surgical tool on the graphical user interface 2000. The device 100 may receive an indication of the selected surgical range (as described in FIG. 2) displayed on the graphical user interface 2000. In response to receiving the indication of the selected surgical range (e.g., selected thickness range), the device 100 may simulate a surgical outcome 3004A-3004C associated with selecting a surgical tool 2010A-2010E (e.g., surgical tool 2010D as shown in FIG. 3) on the graphical user interface 2000. In examples, the surgical tools 2010A-2010E are stapler cartridge types (e.g., surgical stapler reload selections), each of the stapler cartridge types (e.g., surgical stapler reload selections) being desired for use at different surgical ranges (e.g., different tissue thickness ranges), depending on the perfusion preference(s) of the user.

In examples, in response to receiving an indication of the selected surgical range (e.g., selected tissue thickness range), the simulated surgical outcomes 3004A-3004C may represent simulated perfusion outcomes associated with selecting a surgical tool (e.g., stapler cartridge type). Each of the simulated surgical outcomes 3004A-3004C may be presented in a different color so the user can easily differentiate between them. In examples, 3004A may represent "minimal perfusion," 3004B may represent "low perfusion," and 3004C may represent "moderate perfusion." "Minimal perfusion" may be the surgical outcome simulated if the selected surgical range (e.g., selected tissue thickness range) is near the upper end of the surgical range of a surgical tool 2010A-2010E (e.g., a 3.3 mm selected tissue thickness range would be at the upper end of the tissue thickness range 2.0 mm-3.3 mm for surgical tool 2010D, as shown in FIG. 3). "Low perfusion" may the surgical outcome simulated if the selected surgical range (e.g., selected tissue thickness range) is near the middle of the surgical range of the surgical tool 2010A-2010E (e.g., a 2.6 mm selected tissue thickness range would be near the middle of the tissue thickness range 2.0 mm-3.3 mm for the surgical tool 2010D). "Moderate perfusion" may be the surgical outcome simulated if the selected surgical range (e.g., selected tissue thickness range) is near the lower end of the surgical range of the surgical tool 2010A-2010E (e.g., a 2.0 mm selected tissue thickness range would be near the lower end of the tissue thickness range 2.0 mm-3.3 mm for surgical tool 2010D). Although three simulated surgical outcomes are shown in FIG. 3, there may be any number of simulated surgical outcomes.

In examples, 3004A (e.g., "minimal perfusion") may be the simulated surgical outcome at the selected surgical range (e.g., selected tissue thickness) associated with selecting a surgical tool (e.g., stapler cartridge type). For example, if the selected surgical range is 3.3 mm (as shown in FIG. 3) and the selected surgical tool is 2010D with a tissue thickness range between 2.0 mm and 3.3 mm (as shown in FIG. 3), 3004A (e.g., "minimal perfusion") may be the simulated surgical outcome (e.g., simulated perfusion outcome). In examples, 3004B (e.g., "low perfusion") may be the simulated surgical outcome at the selected surgical range (e.g., selected tissue thickness) associated with selecting a surgical tool (e.g., stapler cartridge type). For example, if the selected surgical range is 3.3 mm and the selected surgical tool is 2010E with a tissue thickness range between 2.3 mm and 4.0 mm, 3004B (e.g., "low perfusion") may be the simulated surgical outcome (e.g., simulated perfusion outcome). In examples, 3004C (e.g., "moderate perfusion") may be the simulated surgical outcome at the selected surgical range (e.g., selected tissue thickness) associated with selecting a surgical tool (e.g., stapler cartridge type). For example, if the selected surgical range is 1.9 mm and the selected surgical tool is 2010C with a tissue thickness range between 1.8 mm and 3.0 mm, 3004C (e.g., "moderate perfusion") may the simulated surgical outcome (e.g., simulated perfusion outcome). The simulated surgical outcomes (e.g., perfusion outcomes) 3004A-3004C may help a user select their desired surgical tool (e.g., desired stapler cartridge) at the selected surgical range (e.g., selected tissue thickness range) for a desired perfusion outcome (e.g., "minimal perfusion," "low perfusion," "moderate perfusion").

The device 100 may receive an indication of the selected surgical tool (e.g., selected stapler cartridge or selected surgical stapler reload type) at the surgical tool selection point on the graphical user interface 2000. In examples, the user may select the selection tool button 3002 to indicate the selection of a surgical tool (e.g., surgical tool 2010D in FIG. 3) at the surgical selection point.

Figure 4:
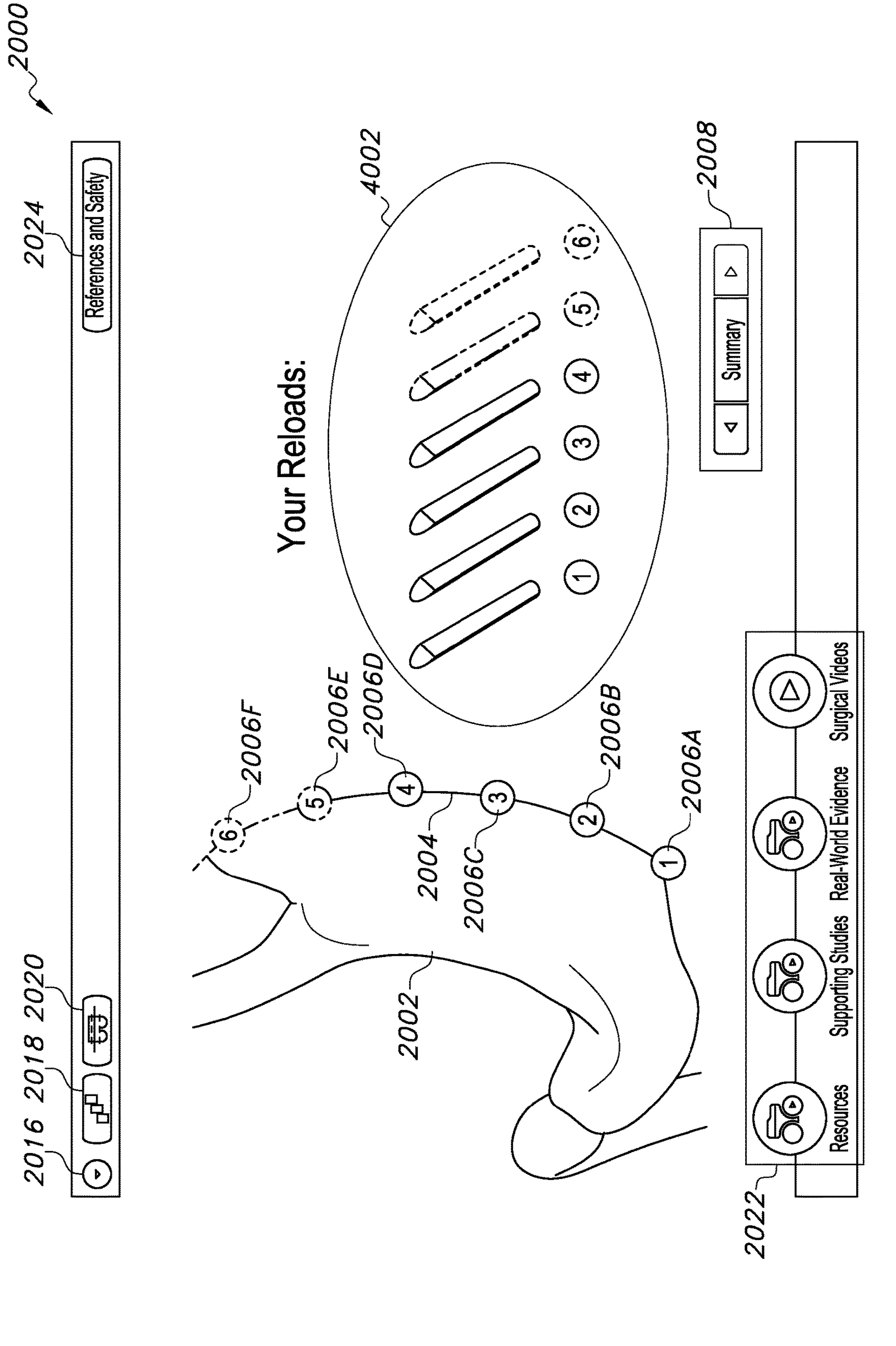
FIG. 4 illustrates an example of generating a selected surgical tool for each selection point on the graphical user interface.

FIG. 4 illustrates an example of generating a surgical plan for each the surgical tool selection point on the path 2004 for simulating the surgical activity displayed on the graphical user interface 2000. In response to receiving the indication of the selected surgical tool of the surgical tools 2010A-2010E at the surgical tool selection point of the surgical tool selection points 2006A-2006F, the device 100 may generate the surgical plan for the surgical tool selection points 2006A-2006F on the path 2004 for performing the surgical activity. The generated surgical plan for the surgical tool selection points 2006A-2006F may be displayed at summary section 4002 on the graphical user interface 2000.

In examples, summary section 4002 on the graphical user interface 2000 may be represented as "Your Reloads," which may generate the surgical plan for the surgical tool selection pints 2006A-2006F. The surgical plan may indicate the type of surgical tool (e.g., surgical stapler cartridge type) selected at each of the surgical tool selection points 2006A-2006F. Although six surgical tool selection points 2006A-2006F are shown in FIG. 4, there may be any number of surgical tool selection points. As shown in FIG. 4, the user may use the arrows on the surgical point selector 2008 to select "Summary." If "Summary" is selected, the graphical user interface 2000 may generate the surgical tool selection point numbers (e.g., "1" for surgical tool selection point 2006A, "2" for surgical tool selection point 2006B, "3" for surgical tool selection point 2006C, "4" for surgical tool selection point 2006D, "5" for surgical tool selection point 2006E, "6" for surgical tool selection point 2006F") and the type of surgical tool selected above each of the numbers within the summary section 4002. The summary section 4002 may provide the user with an overview of (e.g., all of) the simulated selected surgical tools for performing the surgical activity along with the path 2004. In examples, the summary selection 4002 may provide the user with an overview of (e.g., all of) the simulated stapler cartridge types (e.g., surgical stapler reload types) to use for performing a laparoscopic sleeve gastrectomy along a staple line path for cutting a portion of anatomy (e.g., a portion of the stomach). As shown in FIG.

4, the summary section 4002 may provide the user with an overview of six (e.g., all six) of the selected surgical tools 2010A-2010E (e.g., stapler cartridge types or surgical stapler reload types) at the six surgical tool selection points 2006A-2006F.

In examples, a control signal may be generated for performing the surgical activity along the path 2004. The control signal may include an indication of the selected surgical tools at the surgical tool selection points. The control signal may include the surgical plan for the surgical tool selection points 2006A-2006F on the path 2004 for performing the surgical activity. The surgical plan may include the selected surgical tools of the surgical tools 2010A-2010E at the surgical tool selection points 2006A-2006F, as indicated in the summary section 4002. In examples, the control signal may indicate the simulated stapler cartridge types (e.g., surgical stapler reload types) to use for performing a laparoscopic sleeve gastrectomy along a staple line path for cutting a portion of anatomy (e.g., a portion of the stomach). The control signal may be configured to indicate the selected surgical tools 2010A-2010E (e.g., stapler cartridge types or surgical stapler reload types) at the six surgical tool selection points 2006A-2006F. The control signal may be sent to a simulator outside of the device 100. The simulator may simulate performing the surgical activity along the path 2004 for performing the surgical activity. The simulator may use the selected surgical tools at the surgical tool selection points 2006A-2006F, based on the information provided by the control signal. The simulator may be used to simulate a surgery.

The control signal may be sent to a surgical control system. For example, the control signal may be configured to prompt the surgeon or the surgeon's assistant to use the appropriate surgical tools at the responding surgical tool selection points. The control signal may be configured to control an autonomous surgical task. The autonomous surgical task may perform the surgical activity using the simulated path 2004. The surgery may use the selected simulated surgical tools at the surgical tool selection points 2006A-2006F, based on the control signal.

Figure 5A:
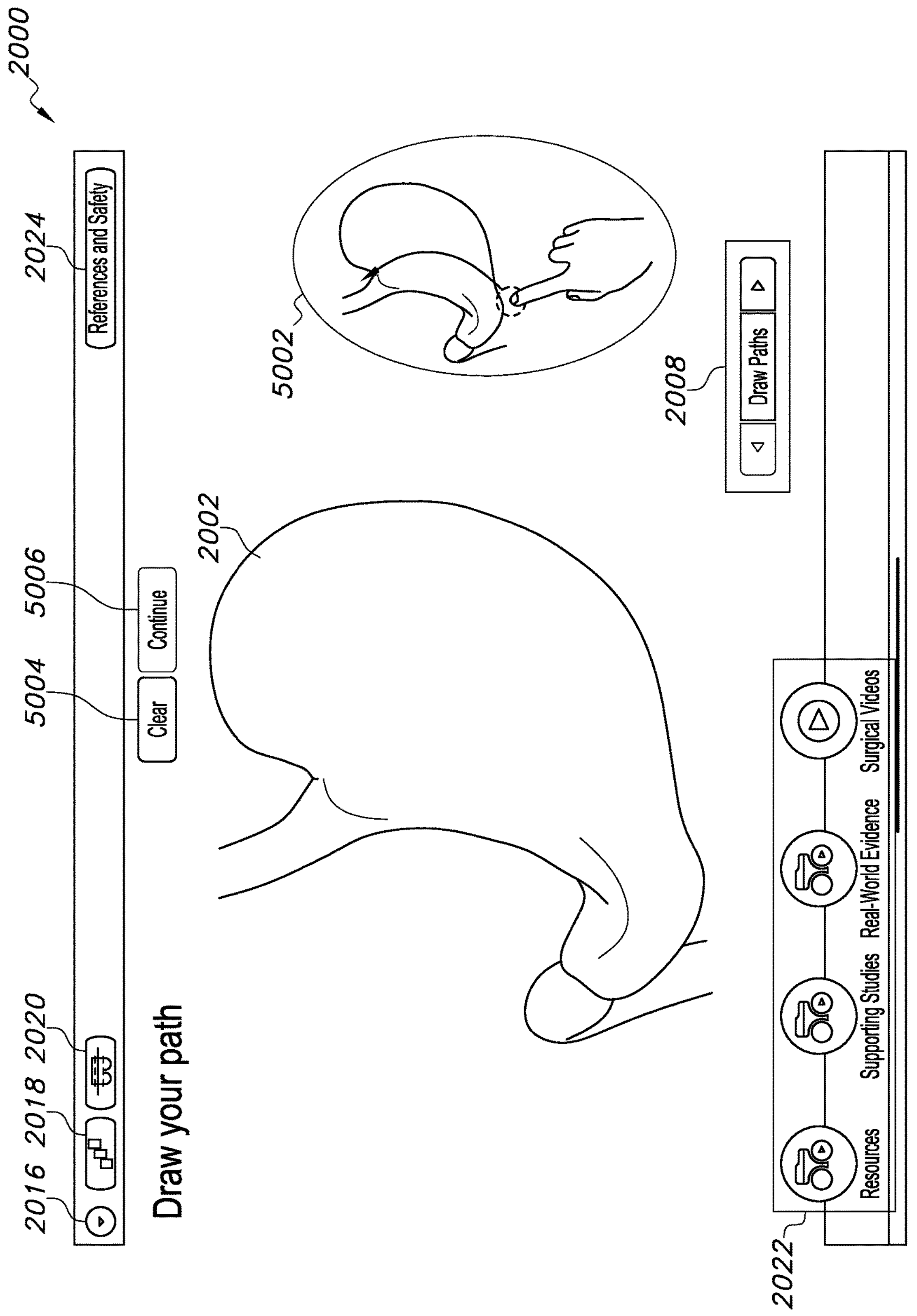
FIGS. 5A-5B illustrate an example of simulating a path on the graphical user interface.
Figure 5B:
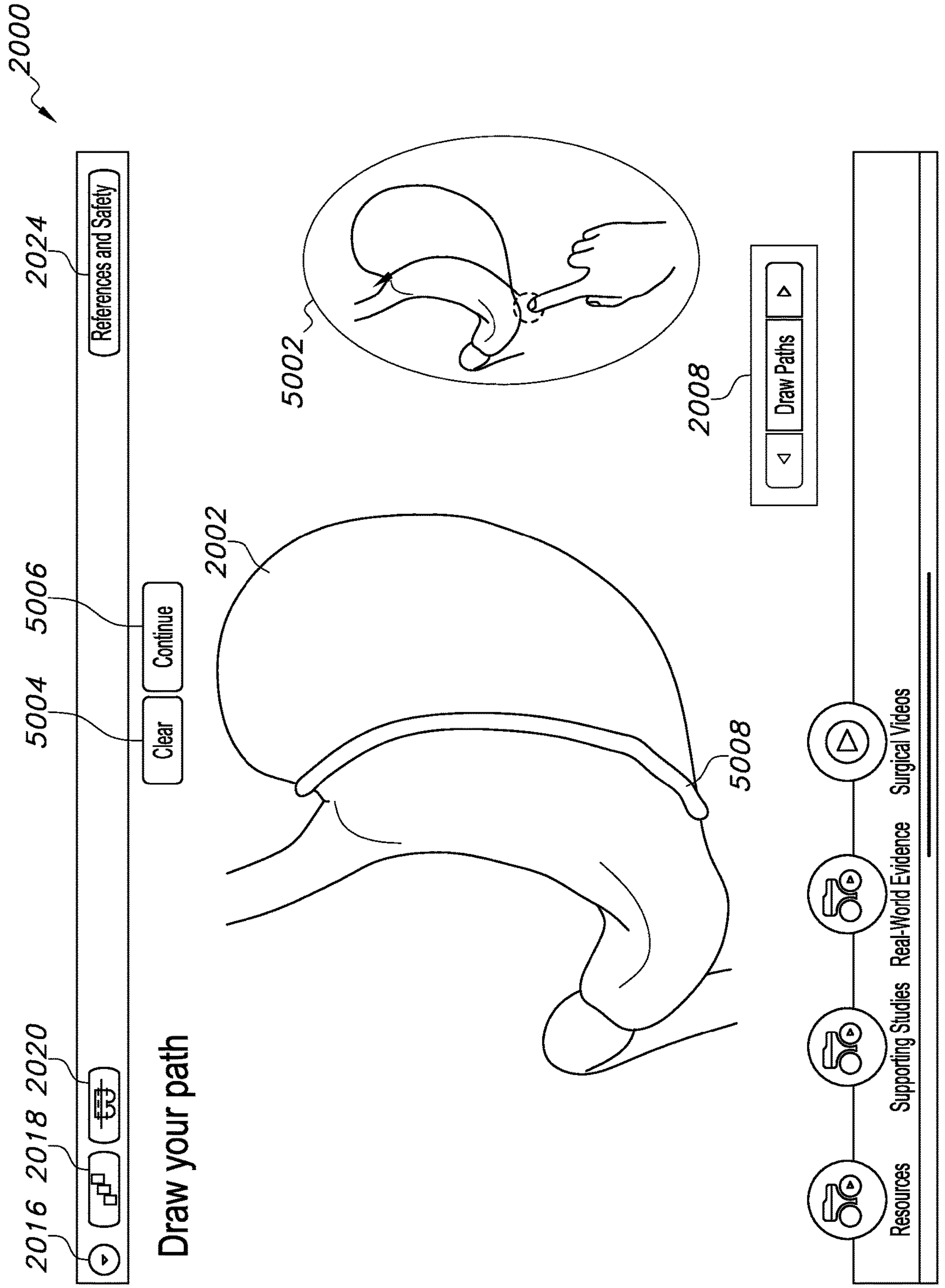

FIGS. 5A-5B illustrate an example of simulating a path on the graphical user interface 2000. The device 100 may be configured to enable a user to draw on the first graphical representation 2002 of the graphical user interface 2000. The first graphical representation 2002 may represent a portion of anatomy (e.g., a portion of a stomach). To draw on the first graphical representation 2002, the user may use the arrows on the surgical point selector 2008 to select "Draw Paths." As shown in FIG. 5A, if "Draw Paths" is selected on the surgical point selector 2008, the drawing symbol 5002 may be displayed on the graphical user interface 2000. The drawing symbol 5002 may inform the user that they can draw on the first graphical representation 2002.

As shown in FIG. 5B, the user may draw a drawn path 5008 over the first graphical representation 2002. In examples, the user may hand draw the drawn path 5008 via a touch screen, the user may drag their mouse to draw the drawn path 5008, or other methods may be used to draw the drawn path 5008. The device 100 may receive an indication from the user of the drawn path 5008. In response to receive the indication from the user of the drawn path 5008, the device 100 may superimpose the drawn path 5008 via a second graphical representation over the first graphical representation 2002 (e.g., as shown in FIG. 5B) on the graphical user interface 2000. The user may select the clear button 5004 to clear the drawn path 5008, and thereafter start over and draw another path. The user may select the continue button 5006, which may prompt the device 100 to segment the drawn path 5008 into multiple segments (e.g., as described above in FIG. 2). Each of the segments may be separated by the starting point (e.g., "1" in FIG. 2) and identified intersection points (e.g., "2-6 in FIG. 2), which may be surgical tool selection points (e.g., as described above in FIG. 2).

FIG. 6 illustrates an example of simulating a reinforcement range associated with a surgical range on the graphical user interface 2000. The reinforcement toggle 2020 may trigger the device 100 to calculate a reinforced surgical range 6001 based on the selected surgical range and a reinforcement range 6002 on the graphical user interface 2000. In response to receiving the indication of the calculated reinforced surgical range 6001, the device 100 may display the reinforced surgical range 6001 along the first axis (e.g., vertical axis) representing the surgical range 2014. The reinforced surgical range 6001 may within the tissue thicknesses associated with different surgical tools 2010A-2010E than the selected surgical range. The device 100 may simulate a surgical outcome 3004A-3004C (e.g., as described in FIG. 3) associated with selecting a surgical tool 2010A-2010E on the graphical user interface (e.g., along the second axis or horizontal axis). In examples, the reinforced surgical range 6001 may be a reinforced tissue thickness range. In examples, in response to receiving an indication of the reinforced surgical range 6001 (e.g., the reinforced tissue thickness range), the simulated surgical outcomes 3004A-3004C may represent simulated perfusion outcomes associated with selecting a stapler cartridge type. The reinforced surgical range 6001 may result in different surgical outcomes 3004A-3004C than the surgical outcomes 3004A-3004C associated with the selected surgical range.

In examples, 3004A (e.g., "minimal perfusion") may be the simulated surgical outcome at the reinforced surgical range (e.g., the reinforced tissue thickness range) associated with selecting a surgical tool (e.g., stapler cartridge type). In examples, 3004B (e.g., "low perfusion") may be the simulated surgical outcome at the reinforced surgical range (e.g., reinforced tissue thickness range) associated with selecting a surgical tool (e.g., stapler cartridge type). In examples, 3004C (e.g., "moderate perfusion") may be the simulated surgical outcome at the reinforced surgical range (e.g., reinforced tissue thickness range) associated with selecting a surgical tool (e.g., stapler cartridge type). The simulated surgical outcomes 3004A-3004C may help a user select their desired surgical tool (e.g., desired stapler cartridge) for a desired perfusion outcome (e.g., "minimal perfusion," "low perfusion," "moderate perfusion").

FIG. 7 illustrates an example of presenting a second set of surgical tools (e.g., an alternative set of surgical tools) to select from on the graphical user interface 2000. The surgical tool toggle 2018 may trigger the device 100 to present a second set of surgical tools 7002A-7002C to select from at the selected surgical tool selection point 2006A-2006F, where the surgical tools 2010A-2010E is a first set of surgical tools 2010A-2010E. The second set of surgical tools 7002A-7002C may represent a second set of stapler cartridge types corresponding to different tissue thickness ranges than the first set of surgical tools 2010A-2010E. Each of the second set of surgical tools 7002A-7002C may be presented in a different color so the user can easily differentiate between them.

Each of the second set of surgical tools 7002A-7002C presented along the second axis (e.g., the horizontal axis) may have a tissue thickness range. The tissue thickness range for each of the second set of surgical tools 7002A-

7002C may include a lower limit and an upper limit, corresponding to the surgical range 2014 presented along the first axis (e.g., the vertical axis). The tissue thickness range for each of the surgical tools 7002A-7002C may help the user to select the surgical tool 7002A-7002C based on the selected surgical range (e.g., the selected tissue thickness range).

The device 100 may receive an indication of the selected surgical range (as described in FIG. 2) on the graphical user interface 2000. In response to receiving the indication of the selected surgical range, the device 100 may simulate a surgical outcome 3004A-3004C (e.g., as described in FIG. 3) associated with selecting a surgical tool of the second set of surgical tools 7002A-7002C. In examples, in response to receiving an indication of a selected surgical range (e.g., selected tissue thickness range), the simulated surgical outcomes 3004A-3004C may represent simulated perfusion outcomes associated with selecting a stapler cartridge type of the second set of stapler cartridge types (e.g., surgical stapler reload selections) at the selected surgical range (e.g., tissue thickness range). In examples, 3004A may represent "minimal perfusion," 3004B may represent "low perfusion," and 3004C may represent "moderate perfusion."

The device 100 may receive an indication of the selected surgical tool of the second surgical tools 7002A-7002C at the surgical selection point 2006A-2006F on the graphical user interface 2000. In examples, the user may select the selection tool button 3002 (e.g., as described above in FIG. 3) to indicate the selection of a surgical tool of the second set of surgical tools 7002A-7002C at the surgical selection point 2006A-2006F.

In response to receiving the indication of the selected surgical tool of the second set of surgical tools 7002A-7002C at the surgical selection point 2006A-2006F, the device 100 may generate the surgical plan for the surgical tool selection points 2006A-2006F on the path 2004 for performing the surgical activity. The surgical plan may include the selected surgical tool 7002A-7002C at each of the selection points 2006A-2006F, which may be displayed at summary section 4002 on the graphical user interface 2000 (e.g., as described in FIG. 4). The device 100 may convert the selected surgical tools of the second set of surgical tools 7002A-7002C at each of the surgical tool selection points 2006A-2006F to surgical tools of the first set of surgical tools 2010A-2010E.

Although features and elements described above are described in particular combinations, each feature or element may be used alone without the other features and elements of the preferred embodiments, or in various combinations with or without other features and elements.

The processes described above may be implemented in a computer program, software, and/or firmware incorporated in a computer-readable medium for execution by a computer and/or processor. Examples of computer-readable media include, but are not limited to, electronic signals (transmitted over wired and/or wireless connections) and/or computer-readable storage media. Examples of computer-readable storage media include, but are not limited to, a read only memory (ROM), a random access memory (RAM), a register, cache memory, semiconductor memory devices, magnetic media such as, but not limited to, internal hard disks and removable disks, magneto-optical media, and/or optical media such as compact disc (CD)-ROM disks, and/or digital versatile disks (DVDs).

The invention claimed is:

1. A device for simulating a surgical activity, comprising:
a processor configured to:
present a first graphical representation of a portion of anatomy;
simulate a path for the surgical activity via a second graphical representation, wherein the simulated path is superimposed over the first graphical representation;
determine a plurality of surgical tool selection points associated with selecting a plurality of surgical tools on the simulated path for the surgical activity;
display the plurality of surgical tool selection points associated with selecting the plurality of surgical tools on the simulated path for the surgical activity;
present a surgical range and the plurality of surgical tools to select from at a surgical tool selection point of the plurality of surgical tool selection points;
receive an indication of a selected surgical range and a selected surgical tool; determine a simulated surgical outcome based on the selected surgical range and the selected surgical tool at the surgical tool selection point; and
display the simulated surgical outcome based on the selected surgical range and the selected surgical tool at the surgical tool selection point.

2. The device of claim 1, wherein the simulated surgical outcome is a simulated perfusion outcome and the plurality of surgical tools is a plurality of staple cartridge types, and wherein the processor is further configured to:
determine the simulated perfusion outcome based on the selected surgical range and the selected surgical tool at the surgical tool selection point; and
display the simulated perfusion outcome based on the selected surgical range and the selected surgical tool at the surgical tool selection point.

3. The device of claim 1, wherein the processor is further configured to:
display a reinforcement range associated with the selected surgical range;
calculate a reinforced surgical range based on the selected surgical range and the reinforcement range, wherein the simulated surgical outcome is determined based on the reinforced surgical range; and
display the calculated reinforced surgical range.

4. The device of claim 1, wherein the plurality of surgical tools is a first plurality of surgical tools, the simulated surgical outcome is a first simulated surgical outcome, and the processor is further configured to:
present a second plurality of surgical tools to select from at the surgical tool selection point;
in response to receiving the indication of the selected surgical range, display a second simulated surgical outcome associated with selecting a surgical tool of the second plurality of surgical tools at the surgical tool selection point;
receive an indication of a selected surgical tool of the second plurality of surgical tools;
in response to receiving the indication of the selected surgical tool of the second plurality of surgical tools, generate a surgical plan for the plurality of surgical tool selection points on the path of the surgical activity; and
display the generated surgical plan.

5. The device of claim 4, wherein the processor is further configured to:
convert the selected surgical tool of the second plurality of surgical tools to a surgical tool of the first plurality of surgical tools at the surgical tool selection point; and
display the converted surgical tool.

6. The device of claim 1, wherein the processor is further configured to:

present a first axis configured to represent the surgical range to select from, the first axis having a slider, wherein the indication of the selected surgical range is received via the slider; and based on the selected surgical range selected via the slider, display a simulated surgical outcome associated with selecting a surgical tool of the plurality of surgical tools at the surgical tool selection point, wherein the plurality of surgical tools is displayed along a second axis.

7. The device of claim 1, wherein the surgical activity is a cutting path, the plurality of surgical tools is a plurality of staple cartridge types, and the surgical range is a tissue thickness range, and wherein the processor is further configured to:

determine a plurality of surgical tool selection points associated with selecting a plurality of staple cartridge types on the cutting path;

display the plurality of surgical tool selection points associated with selecting the plurality of staple cartridge types on the cutting path;

present the tissue thickness range to select from at a surgical tool selection point of the plurality of surgical tool selection points;

receive an indication of a selected tissue thickness range;

in response to receiving the indication of the selected tissue thickness range, display a simulated surgical outcome associated with selecting a staple cartridge type of the plurality of staple cartridge types at the surgical tool selection point;

receive an indication of a selected staple cartridge type of the plurality of staple cartridge types;

in response to receiving the indication of the selected staple cartridge type of the plurality of staple cartridge types, generate a surgical plan for the plurality of surgical tool selection points on the path of the surgical activity; and display the generated surgical plan.

8. The device of claim 1, wherein the processor is further configured to:

segment the path into six segments based on the simulated path for the surgical activity via a second graphical representation;

identify a start point and five intersection points between the six segments as the plurality of surgical tool selection points;

receive an indication of a selected surgical tool of the plurality of surgical tools;

in response to receiving the indication of the selected surgical tool of the plurality of surgical tools, generate a surgical plan for the plurality of surgical tool selection points on the path of the surgical activity; and display the generated surgical plan.

9. The device of claim 1, wherein the processor is further configured to:

present a graphical user interface configured to enable a user to draw on the first graphical representation of a portion of anatomy;

receive an indication from the user of a drawn path on the first graphical representation of the portion of anatomy; and superimpose the drawn path over the first graphical representation of the portion of anatomy.

10. A method for simulating a surgical activity, the method comprising:

presenting a first graphical representation of a portion of anatomy;

simulating a path for the surgical activity via a second graphical representation, wherein the simulated path is superimposed over the first graphical representation;

determining a plurality of surgical tool selection points associated with selecting a plurality of surgical tools on the simulated path for the surgical activity;

displaying the plurality of surgical tool selection points associated with selecting the plurality of surgical tools on the simulated path for the surgical activity;

presenting a surgical range and the plurality of surgical tools to select from at a surgical tool selection point of the plurality of surgical tool selection points;

receiving an indication of a selected surgical range and a selected surgical tool; determining a simulated surgical outcome based on the selected surgical range and the selected surgical tool at the surgical tool selection point; and displaying the simulated surgical outcome based on the selected surgical range and the selected surgical tool at the surgical tool selection point.

11. The method of claim 10, wherein the simulated surgical outcome is a simulated perfusion outcome and the plurality of surgical tools is a plurality of staple cartridge types, further configured to:

determining the simulated perfusion outcome based on the selected surgical range and the selected surgical tool at the surgical tool selection point; and displaying the simulated perfusion outcome based on the selected surgical range and the selected surgical tool at the surgical tool selection point.

12. The method of claim 10, further comprising:

displaying a reinforcement range associated with the selected surgical range;

calculating a reinforced surgical range based on the selected surgical range and the reinforcement range, wherein the simulated surgical outcome is determined based on the reinforced surgical range; and displaying the calculated reinforced surgical range.

13. The method of claim 10, wherein the plurality of surgical tools is a first plurality of surgical tools, and wherein the simulated surgical outcome is a first simulated surgical outcome, further comprising:

presenting a second plurality of surgical tools to select from at the surgical tool selection point;

in response to receiving the indication of the selected surgical range, displaying a second simulated surgical outcome associated with selecting a surgical tool of the second plurality of surgical tools at the surgical tool selection point;

receiving an indication of a selected surgical tool of the second plurality of surgical tools;

in response to receiving the indication of the selected surgical tool of the second plurality of surgical tools, generating a surgical plan for the plurality of surgical tool selection points on the path of the surgical activity; and displaying the generated surgical plan.

14. The method of claim 13, further comprising:

converting the selected surgical tool of the second plurality of surgical tools to a surgical tool of the first plurality of surgical tools at the surgical tool selection point; and displaying the converted surgical tool.

15. The method of claim 10, further comprising:

presenting a first axis configured to represent the surgical range to select from, the first axis having a slider, wherein the indication of the selected surgical range is received via the slider; and based on the selected surgical range selected via the slider, displaying a simulated surgical outcome associated with selecting a surgical tool of the plurality of surgical tools at the surgical tool selection point, wherein the plurality of surgical tools is displayed along a second axis.

16. The method of claim 10, wherein the surgical activity is a cutting path, the plurality of surgical tools is a plurality of staple cartridge types, and the surgical range is a tissue thickness range, further configured to:

determining a plurality of surgical tool selection points associated with selecting a plurality of staple cartridge types on the cutting path;

displaying the plurality of surgical tool selection points associated with selecting the plurality of staple cartridge types on the cutting path;

presenting the tissue thickness range to select from at a surgical tool selection point of the plurality of surgical tool selection points;

receiving an indication of a selected tissue thickness range;

in response to receiving the indication of the selected tissue thickness range, displaying a simulated surgical outcome associated with selecting a staple cartridge type of the plurality of staple cartridge types at the surgical tool selection point;

receiving an indication of a selected staple cartridge type of the plurality of staple cartridge types;

in response to receiving the indication of the selected staple cartridge type of the plurality of staple cartridge types, generating a surgical plan for the plurality of surgical tool selection points on the path of the surgical activity; and displaying the generated surgical plan.

17. The method of claim 10, further comprising:

segmenting the path into six segments based on the simulated path for the surgical activity via a second graphical representation;

identifying a start point and five intersection points between the six segments as the plurality of surgical tool selection points;

receiving an indication of a selected surgical tool of the plurality of surgical tools; and in response to receiving the indication of the selected surgical tool of the plurality of surgical tools, generating a surgical plan for the plurality of surgical tool selection points on the path of the surgical activity; and displaying the generated surgical plan.

18. The method of claim 10, further comprising:

presenting a graphical user interface configured to enable a user to draw on the first graphical representation of a portion of anatomy;

receiving an indication from the user of a drawn path on the first graphical representation of the portion of anatomy; and superimposing the drawn path over the first graphical representation of the portion of anatomy.

19. The device of claim 1, wherein the simulated surgical outcome is a perfusion outcome, and wherein the perfusion outcome is one of minimal perfusion, low perfusion, or moderate perfusion.

20. The method of claim 10, wherein the simulated surgical outcome is a perfusion outcome, and wherein the perfusion outcome is one of minimal perfusion, low perfusion, or moderate perfusion.

* * * * *